United States Patent [19]

de Rooij

[11] 3,940,442

[45] Feb. 24, 1976

[54] RECYCLE PROCESS FOR THE PREPARATION AND PROCESSING OF A HYDROXYLAMMONIUM SALT SOLUTION

[75] Inventor: Abraham H. de Rooij, Geleen, Netherlands

[73] Assignee: Stamicarbon B.V., Geleen, Netherlands

[22] Filed: Jan. 17, 1975

[21] Appl. No.: 542,045

Related U.S. Application Data

[63] Continuation-in-part of Ser. No. 95,318, Dec. 4, 1970, abandoned, which is a continuation-in-part of Ser. No. 95,389, Dec. 4, 1970, abandoned.

[30] Foreign Application Priority Data

Dec. 6, 1969 Netherlands.................... 6918366
Dec. 6, 1969 Netherlands.................... 6918367

[52] U.S. Cl.............................. 260/566 A; 423/387
[51] Int. Cl.²........................................ C07C 131/04
[58] Field of Search................. 260/566 A; 423/387

[56] References Cited
UNITED STATES PATENTS 3,335,183  8/1967  de Rooij ...................... 260/566 A
3,429,920  2/1969  de Rooij ...................... 260/566 A Primary Examiner—Gerald A. Schwartz
Attorney, Agent, or Firm—Cushman, Darby & Cushman

[57] ABSTRACT

An improved recycle process for the production of cyclohexanone oxime comprising circulating an acidic, aqueous solution containing phosphoric acid or ammonium bisulphate or a mixture thereof between a hydroxylamine synthesis zone and a cyclohexanone oxime synthesis zone. Nitrate ions are added to the aqueous solution just prior to the hydroxylamine synthesis zone and catalytically reduced with molecular hydrogen. The aqueous solution from the hydroxylamine synthesis zone is then fed to the cyclohexanone oxime synthesis zone along with a ketone. The aqueous solution is then separated from the oxime formed, either (a) treated at an elevated temperature for a sufficient time to decompose any trace amounts of oxime and cyclohexanone or (b) subjected to a stripping step to remove any trace amounts of oxime and cyclohexanone before being recirculated to the hydroxylamine synthesis zone. The oxime formed by this process is a valuable commercial commodity.

5 Claims, 2 Drawing Figures

RECYCLE PROCESS FOR THE PREPARATION AND PROCESSING OF A HYDROXYLAMMONIUM SALT SOLUTION

CROSS-REFERENCE TO RELATED APPLICATIONS

This application is a continuation-in-part of our co-pending earlier applications Ser. No. 95,318 and Ser. No. 95,389, both filed on Dec. 4, 1970 both of which are now abandoned.

BACKGROUND OF THE INVENTION

The present invention relates to an improved recycle process for the preparation and processing of a hydroxylammonium salt solution, and in one embodiment thereof an apparatus used in carrying out the improved process. The hydroxylammonium salts are useful in the known preparation of oximes from ketones, in particular in the preparation of cyclohexanone oxime from cyclohexanone.

In a known recycle process for the production of hydroxylammonium salt solutions, an acidic, buffered, aqueous reaction medium containing buffer acids or acidic salts, for example phosphoric acid or bisulphate, respectively, and buffer salts derived from these acids, is continuously recycled between a hydroxylammonium salt synthesis zone, in which nitrate ions are catalytically reduced with molecular $H_2$ to hydroxylamine, and an oximation zone. The nitrate ions, which are consumed in the hydroxylammonium salts synthesis zone, are added to the recycling aqueous reaction medium just before the hydroxylammonium salt synthesis zone. Nitric acid, such as a 60% aqueous solution of nitric acid, is commonly used as the source of nitrate ions. A hydroxylamine, initially formed in the hydroxylamine synthesis zone, reacts with the free buffer acid of the recycling medium to form the corresponding hydroxylammonium salt, and the resulting hydroxylammonium salt solution is then fed to the oximation zone, where the hydroxylammonium salt reacts with a ketone, forming the corresponding oxime, with simultaneous liberation of the acidic, buffered, aqueous reaction medium. The aqueous reaction medium is then freed of the oxime and recycled to the hydroxylammonium salt synthesis zone.

If the hydroxylamine preparation is based on the buffered reaction medium comprising phosphoric acid and nitrate, the chemical reactions occurring during the successive operations can be represented by the following equations:

1. formation of hydroxylammonium salt:

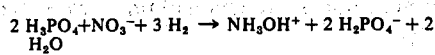

2. formation of cyclohexanone oxime:

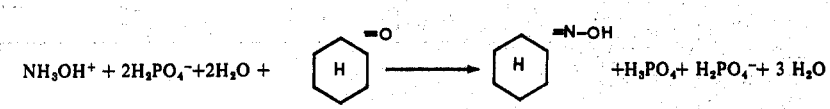

3. addition of $HNO_3$ to replace the nitrate ions which were used in forming the oxime:

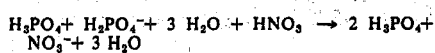

The buffered reaction medium preferably contains phosphoric acid.

The solution formed in step three will, theoretically, have the same composition as the initial solution used for the hydroxylammonium salt formation.

The catalyst used in the reduction of the nitrate ions is a palladium catalyst, generally palladium on a carrier material of carbon or alumina, the carrier material being loaded with from 5–20% wt. of palladium. The activity of the catalyst is adversely affected by the presence of organic substances. In the prior art process, the aqueous reaction medium which is discharged from the cyclohexanone oxime synthesis zone contains residual amounts of cyclohexanone and cyclohexanone oxime. The palladium catalyst is adversely affected by these residual amounts of cyclohexanone and cyclohexanone oxime and ultimately becomes poisoned. Accordingly, it is an object of the present invention to remove these residual amounts of cyclohexanone and cyclohexanone oxime to prevent poisoning of the catalyst.

DETAILED DESCRIPTION OF THE INVENTION

It has now been found that the residual organic compounds such as the oxime or ketones used in the process can be effectively reliably and simply removed according to one embodiment of the invention by (a) heating the liquid discharged from the cyclohexanone oxime synthesis zone to an elevated temperature for such a time that the organic compounds including the oxime are decomposed and oxidized to compounds which do not affect the activity of the catalyst. In another embodiment of the present invention we have found that these residuant organic components are also easily removed by (b) subjecting the liquid discharged from the cyclohexanone oxime synthesis zone to a stripping process whereby the undesired detrimental organic compounds are decomposed and oxidized to compounds not affecting the catalyst activity.

The present invention will be more fully explained with reference to the drawings and the following examples.

IN THE DRAWINGS

The following figures and example relate to the first embodiment (a), as illustrated above.

Figure 1:
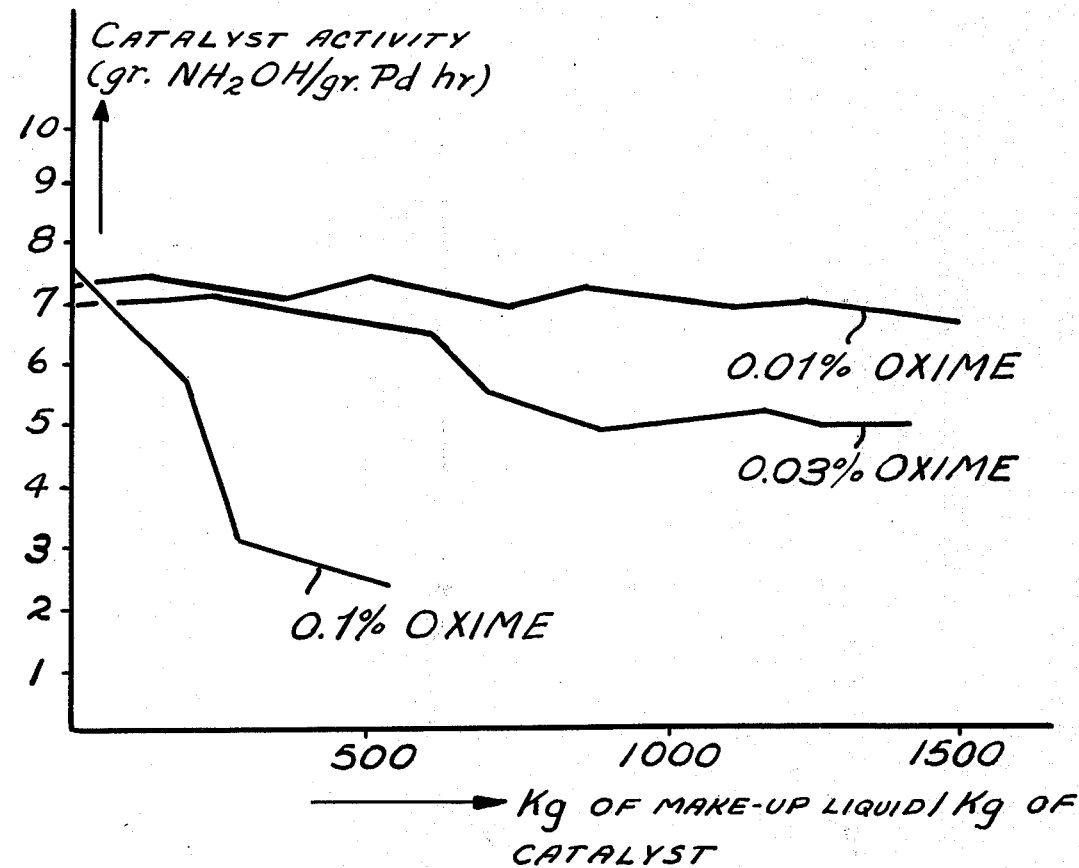
FIG. 1 is a graph showing the effect of varying concentrations of cyclohexanone/oxime on the activity of the palladium catalyst.

The influence of cyclohexanone oxime on the activity of the paladium catalyst is shown in FIG. 1, which represent data from experiments using a catalyst consisting of 5% wt. of palladium on active carbon. The catalyst was used first for the preparation of hydroxylamine by reduction of a solution containing nitrate ions in a phosphoric acid medium, and subsequently the reaction solution containing nitrate ions and phosphoric acid also contained 0.1, 0.03 or 0.01% wt of cyclohexanone oxime.

The decrease in activity of the palladium catalyst, expressed in grams of hydroxylamine per gram of palladium per hour, is shown on the graph of FIG. 1. In FIG. 1, the activity of the catalyst at 1 atm and 25° C. is plotted on the ordinate and the quantity of reaction liquid, in kg, reacted in the presence of 1 kg of catalyst, is shown on the abscissa.

When the reaction liquid is contaminated with 0.1% wt of oxime, the activity decreased to ⅓ of its orginal value after only 500 kg of reactants had contacted the catalyst. A content of 0.03% wt of oxime reduced the activity to 67% of its original value after 1400 kg of reactants contacted the catalyst. When the reaction liquid was contaminated with 0.01% wt of oxime, the activity was almost unchanged after 1500 kg of reaction liquid had contacted the catalyst.

The results shown in FIG. 1 infer that, to prevent catalyst poisoning, the recycled reaction medium, before entering the hydroxylamine synthesis zone, must be almost completely free of ketone and oxime dissolved in it, i.e., the joint content of ketone and oxime must be reduced to a value of not more than 0.02% wt.

As mentioned above, it has now been found that such remnants, i.e., oximes and ketones, can be rendered harmless if, preferably after the nitric acid make-up, the recycle liquid to be returned to the hydroxylamine synthesis zone is heated at such a temperature and for such a time that the compounds impairing the activity of the catalyst are decomposed or oxiidized to compounds which do not affect the activity of the catalyst.

The rate at which the content of the harmful organic compounds is reduced to the desired level (less than 0.02% wt) is not only dependent on the temperature, but also on the composition of the recycle liquid.

If the recycle liquid does not contain free nitric acid but consists of a solution of phosphoric acid and ammonium nitrate, a temperature of 90° C. or higher is necessary for the required decomposition and oxidation to take place within a reasonable time. However, if the recycle liquid contains nitric acid a reaction temperature of between 50° C. and 90° C., dependent on the concentration of nitric acid, is adequate.

The presence of ammonium sulphate in the recycle liquid retards the decomposition of the contaminants to some extent, and a temperature of about 90° C. is preferred even in the presence of nitric acid. To prevent boiling, the temperature should be below 106° C.

EXAMPLE A

The following experiments, in which the composition of the recycle liquid was varied, will further demonstrate the decomposition of cyclohexanone oxime and the dependence of the decomposition reaction on temperature and time.

In all the following experiments the recycle liquid contained 0.05% wt. of cyclohexanone oxime, which as shown above severely impairs the activity of the catalyst. During decomposition it is desirable as shown above to reduce the oxime content to below 0.02% wt., that is a decomposition of at least 60% must be reached for a starting concentration of oxime of 0.05% by weight.

Experiment 1

A liquid compatible for the hydroxylamine synthesis consisting of 200 moles of $H_3PO_4$, 275 moles of $NH_4NO_3$, 3000 moles of $H_2O$ and 0.05 % by weight of oxime, was heated and held in a storage vessel at 75° C. Samples of this liquid were taken at regular intervals to determine the decomposition of the cyclohexanone oxime.

The decomposition as a function of time proceeded as follows:

| Time, h | Decomposition, % |
|---|---|
| 0 | 0 |
| 0.5 | 32.5 |
| 1.0 | 41.6 |
| 2.0 | 50.0 |
| 4.0 | 66.7 |
| 6.0 | 70.0 |

Experiment 2

The same liquid as used in Experiment 1 was now kept at a temperature of 90° C.

The decomposition as a function of time now proceeded as follows:

| Time, h | Decomposition, % |
|---|---|
| 0 | 0 |
| 0.5 | 23 |
| 1 | 60 |
| 2 | 96 |
| 3 | 99 |

Experiment 3

A liquid compatible for the hydroxylamine synthesis of 100 moles of $H_3PO_4$, 80 moles of $NHO_3$, 36 moles $NH_4NO_3$, 1000 moles $H_2O$ and 0.05% by weight oxime, was kept at a temperature of 50° C. Samples were taken at time intervals as in Experiment 1.

The decomposition of cyclohexanone oxime as a function of time proceeded as follows:

| Time, h | Decomposition, % |
|---|---|
| 0 | 0 |
| 0.5 | 23 |
| 1 | 60 |
| 2 | 96 |
| 3 | 99 |

Experiment 4

The same liquid as used in Experiment 3 was now kept at a temperature of 90° C.

The decomposition is a function of time proceeded as follows:

| Time, h | Decomposition, % |
|---|---|
| 0 | 0 |
| 0.25 | 96 |
| 0.50 | 99 |

Experiment 5

A liquid compatible for the hydroxylamine synthesis consisting of 125 moles of $H_3PO_4$, 60 moles of $HNO_3$, 76 moles of $NH_4NO_3$, 40 moles of $(NH_4)_2SO_4$, 1500 moles $H_2O$ and 0.05 % by weight oxime was kept at 50° C.

The decomposition as a function of time proceeded as follows:

| Time, h | Decomposition, % |
|---------|------------------|
| 0       | 0                |
| 0.5     | 12               |
| 1       | 18               |
| 2       | 32               |
| 3       | 46               |
| 4       | 58               |

Experiment 6

The same liquid as used in experiment 5 was now heated at 90 °C. The decomposition as a function of time proceeded as follows:

| Time, h | Decomposition, % |
|---------|------------------|
| 0       | 0                |
| 0.25    | 83               |
| 0.5     | 85               |
| 1       | 87               |
| 2       | 89               |

In the operation of the process according to this invention, the reaction liquid to be recycled can be passed through one or more vessels equipped with heating coils. The vessels are placed before the hydroxylamine synthesis reactor, preferably between the location where the nitrate ions are added and the hydroxylamine synthesis reactor. The total capacity of the vessels must be such that the liquid to be recycled can be kept sufficiently long at the required temperature to effect the desired conversions. For this purpose the buffer tank can, for example, be provided with outlets at various levels, so that the residence time can be influenced by selecting the discharge level.

In general residence times of 3–6 hours will be more than sufficient to effect the desired decrease in oxime content, while under conditions most favorable for the decomposition and oxidation (high temperature, solution containing nitric acid, absence of sulphate) an hour's residence time or even shorter will prove to be sufficient.

Figure 2:
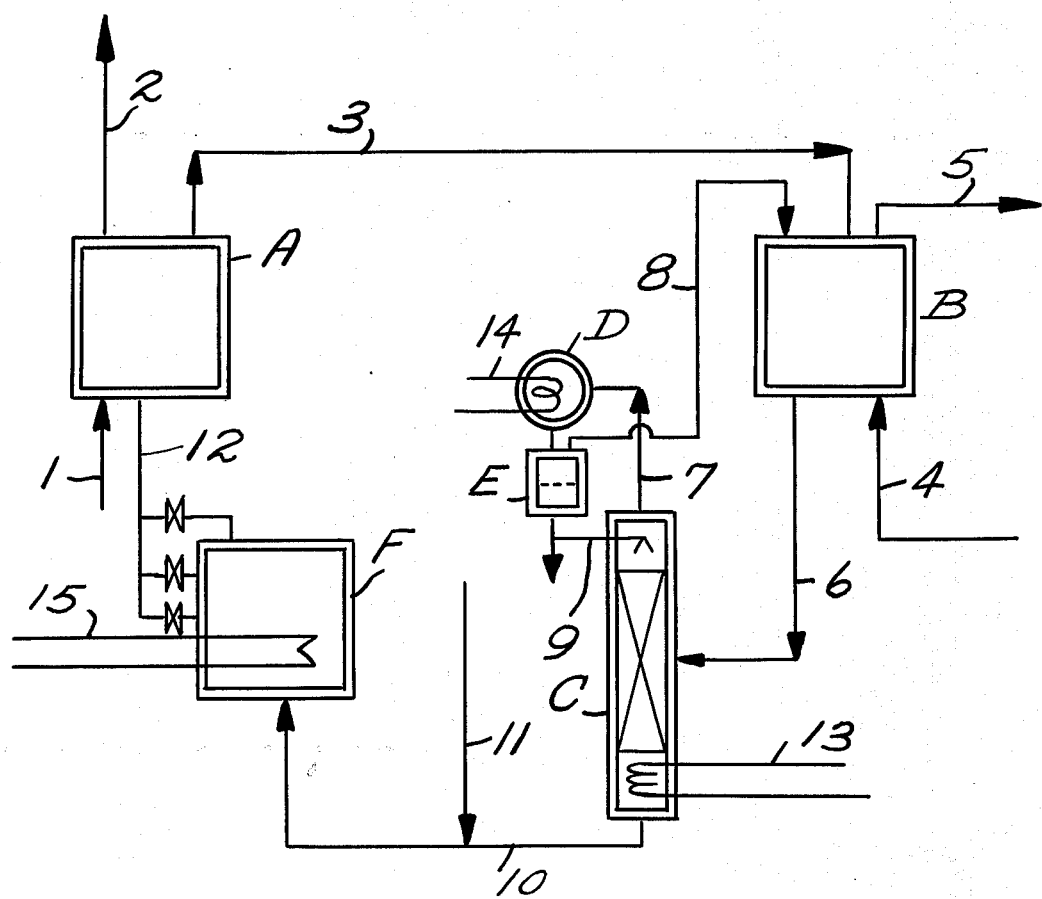
FIG. 2 is a schematic diagram of a preferred embodiment of the process according to the present invention.

One preferred embodiment of the process of this invention is shown diagrammatically in FIG. 2. A and B represent the hydroxylamine synthesis zone and the oxime synthesis zone, respectively. To zone A, containing palladium catalyst, hydrogen is fed via line 1; unreacted hydrogen is discharged, with any other waste gases, via line 2. The reaction medium is fed to zone A through line 12 and after having been enriched in hydroxylamine, is passed to the oxime synthesis zone B via line 3.

The ketone to be converted is fed in an organic solvent (e.g. toluene) to zone B via line 4. The largest part of oxime produced and dissolved in the solvent is removed from the system via line 5.

A recycle liquid which has a reduced hydroxylamine content and contains small quantities of ketone and oxime contaminants is passed to the stripping column C via line 6. In this column oxime is hydrolized to ketone and the ketone thus formed together with the ketone already present is collected in condenser D from the vapor phase together with water vapor.

A condensed water-ketone azeotrope flows to separating vessel E. From separating vessel E ketone is returned to the oxime synthesis zone B via line 8, while the water partly flows back, via line 9, into the top of column C, the remaining water is discarded. Condenser D is cooled with cooling water flowing through cooling tubes 14, while stripping column C receives heat via heating coils 13. The recycle liquid is returned into the hydroxylamine synthesis zone A via line 10, buffer vessel F and line 12.

Via line 11 make-up acid is supplied in the form of nitric acid. The heat treatment according to the invention takes place in buffer vessel F; the required heat is supplied through heating coil 15.

EXAMPLE B

The following examples, illustrate the embodiment of the present invention wherein the cyclohexanone and cyclohexanone oxime are removed by stripping. The influence of cyclohexanone oxime on the activity of the palladium catalyst is shown from experiments using a catalyst consisting of 5% wt. of palladium on active carbon. The catalyst was used first for the preparation of hydroxylamine by reduction of a solution containing nitrate ions in a phosphoric acid medium, and subsequently the reaction solution containing nitrate ions and phosphoric acid also contained 0.1, 0.03 or 0.01% wt. of cyclohexanone oxime.

The decrease in activity of the palladium catalyst, expressed in grams of hydroxylamine per gram of palladium per hour is described below.

When the reaction liquid is contaminated with 0.1% wt. of oxime, the activity decreased to ⅛ of its original value after only 500 kg of reactants had contacted the catalyst. A content of 0.03% wt. of oxime reduced the activity of 67% of its original value after 1400 kg of reactants contacted the catalyst. When the reaction liquid was contaminated with 0.01% wt. of oxime, the activity was almost unchanged after 1500 kg of reaction liquid had contacted the catalyst.

The results demonstrate that, to prevent catalyst poisoning, the recycled reaction medium, before entering the hydroxylamine synthesis zone, must be almost completely free of ketone and oxime dissolved in it, i.e., the joint content of ketone and oxime must be reduced to a value of not more than 0.02% wt.

As mentioned above, it has now been found that such remnants, i.e., oximes and ketones, can be rendered harmless if the recycle liquid to be returned to the hydroxylamine synthesis zone is treated to a stripping step for such a time that the compounds impairing the activity of the catalyst are removed.

Cyclohexanone has a higher volatility than cyclohexanone oxime and in addition the oxime is formed from cyclohexanone by a reaction having an equilibrium which is shifted to the cyclohexanone in an acid medium. It would thus appear to be more advantageous to carry out the stripping treatment when the solution is most acid, i.e., after the nitrate ions have been added to the aqueous reaction medium.

Contrary to expectation, however, it has been unexpectably found that removal of the organic contaminants from the aqueous recycle liquid by stripping is better accomplished prior to the addition of nitrate ions. The explanation of this phenomena might be that with the least acidic medium, hardly any oxidation and decomposition of the cyclohexanone and cyclohexanone oxime takes place. In the more acidic medium, the decomposition of cyclohexanone and cyclohexanone oxime is more prevalent and as a result the cyclohexanone and cyclohexanone oxime are decomposed to less volatile organic compounds which are not removed by the stripping treatment. These less volatile organic compounds continue to increase as the aqueous medium is recycled and ultimately tend to impair the acitivity of the palladium catalyst.

The present invention is, therefore, preferably accomplished by stripping the aqueous solution coming from the oxime synthesis zone before nitrate ions are added to the solution. From the stripping process the solution is recycled back to the hydroxylamine synthesis zone with the nitrate ions being added to the solution. From the stripping process the solution is recycled back to the hydroxylamine synthesis zone with the nitrate ions being added to the recycle medium just prior to the hydroxylamine synthesis zone. The stripping step removes remnants of cyclohexanone and cyclohexanone oxime contained in the aqueous solution coming from the oxime synthesis zone which impair the activity of the palladium catalyst used in the hydroxylamine synthesis zone.

The following examples further demonstrate that the ultimate carbon containing compounds of the recycle liquid, which can impair the activity of the palladium catalyst, is considerably lowered when the nitrate ion addition takes place after the stripping treatment. In addition, the examples demonstrate the general reduction of cyclohexanone and cyclohexanone oxime according to the present invention.

EXAMPLE B-1

Nitric acid was added to the recycle liquid before any stripping treatment had been performed on the recycle liquid. The aqueous solution coming from the oxime synthesis zone comprised:

11.3% by weight $H_3PO_4$
16.5% by weight $NH_4NO_3$
11.1% by weight $NH_4H_2PO_4$
61.0% by weight $H_2O$
0.1% by weight cyclohexanone and cyclohexanone oxime
0.064% by weight of free carbon The nitrate ions were added to this solution in the form of aqueous nitric acid having 55% by weight concentration of $HNO_3$. The nitric acid was added in such quantity that the mono-ammonium phosphate present in the recycle solution was converted into ammonium nitrate and phosphoric acid.

The resulting solution was stripped in a distilling column at atmospheric pressure.

Analysis of samples taken at varying time intervals during the stripping process were made to determine the amount of cyclohexanone and cyclohexanone oxime present as well as the total free carbon present. These results are shown in Table I.

Table I

| time (min.) | % wt. cyclohexanone oxime and cyclohexanone | % wt. C. |
|---|---|---|
| 0 | 0.1 | 0.064 |
| 15 | 0.015 | 0.033 |
| 30 | 0.003 | 0.024 |
| 45 | 0.003 | 0.022 |

As can be seen, the total amount of cyclohexanone and cyclohexanone oxime of the solution is reduced to an insignificant amount after being stripped for only 15 minutes and nearly removed completely after 30 minutes. After 30 minutes of stripping only 3 percent of the total cyclohexanone oxime and cyclohexanone remain. However, the total carbon containing compounds, as illustrated by the weight percent carbon in the solution do not decrease at a rate equivalent to the reduction of cyclohexanone oxime and cyclohexanone. After 30 minutes of stripping approximately 38% of the carbon still remains in the solution.

EXAMPLE B-2

The aqueous solution coming from the oxime synthesis zone as in Example B-1 was stripped without having any nitric acid added to it. The results of analysis of samples taken at varying time intervals similar to those in Example B-1 are shown in Table II.

Table II

| % wt. cyclohexanone oxime and cyclohexanone | % wt. C. |
|---|---|
| 0.1 | 0.064 |
| 0.015 | 0.020 |
| 0.003 | 0.005 |
| 0.003 | 0.005 |

As can be seen, the cyclohexanone and cyclohexanone oxime content is reduced similarly to that shown in Example B-1. However, the total amount of carbon containing compounds remaining in the solution, as is evidenced by the percent carbon in the solution, is reduced considerably more than was done in Example B-1. After 30 minutes of stripping only approximately 7% of the carbon content remains in the solution compared to approximately 38% remaining in the solution in Example B-1.

What is claimed:

1. In a process for producing cyclohexanone oxime in which a buffered, acidic reaction medium comprising an aqueous solution containing phosphoric acid, or ammonium bisulphate is cycled from a hydroxylamine synthesis zone to a cyclohexanone oxime synthesis zone, and back to the hydroxylamine synthesis zone, wherein nitrate ions are obtained in said solution by addition of nitric acid to said solution just prior to introduction into the hydroxylamine synthesis zone and molecular hydrogen is added to the hydroxylamine synthesis zone, said nitrate ions being catalytically reduced to hydroxylamine with said molecular hydrogen in the presence of a supported palladium metal catalyst contained in the hydroxylamine synthesis zone, the solution rich in hydroxylamine from the hydroxylamine synthesis zone is fed with cyclohexanone to said cyclohexanone oxime synthesis zone wherein the hydroxylamine and the cyclohexanone react with each other to form cyclohexanone oxime, separating the cyclohexanone oxime and unreacted cyclohexanone from said solution and recycling said solution back to said hydroxylamine synthesis zone, the improvement of substantially preventing the poisoning of said palladium catalyst consisting of reducing residual amounts of cyclohexanone and cyclohexanone oxime present in the solution after removal of the cyclohexanone oxime produced in the cyclohexanone oxime synthesis zone by heating said solution being recycled from the cyclohexanone oxime synthesis zone to the hydroxylamine synthesis zone to an elevated temperature in the range of 50° to 106° C. for a time sufficiently long enough so that residual amounts of cyclohexanone and cyclohexanone oxime are substantially reduced to below 0.02% by weight.

2. A process as claimed in claim 1 wherein the nitrate ions are added to the solution being recycled from the cyclohexanone oxime synthesis zone to the hydroxylamine synthesis zone prior to the heating of said solution.

3. A process as claimed in claim 2 wherein after the nitrate ions are added the solution contains phosphoric acid, ammonium nitrate and water, and wherein the heat treatment takes places at a temperature of at least 90° C.

4. A process as claimed in claim 1 wherein after the nitrate ions are added the solution contains phosphoric acid, nitric acid, ammonium nitrate, water and soluble or insoluble sulphates, and wherein the heat treatment takes place at a temperature of at least 50° C.

5. In a process for producing cyclohexanone oxime in which a buffered, acidic reaction medium comprising an aqueous solution containing phosphoric acid or ammonium bisulphate is cycled from a hydroxylamine synthesis zone to a cyclohexanone oxime synthesis zone and back to the hydroxyl amine synthesis zone, wherein nitrate ions are obtained in said solution by addition of nitric acid to said solution just prior to introduction into the hydroxylamine synthesis zone and molecular hydrogen is added to the hydroxylamine synthesis zone, said nitrate ions being catalytically reduced to hydroxylamine with said molecular hydrogen in the presence of a supported palladium metal catalyst contained in the hydroxylamine synthesis zone, the solution rich in hydroxylamine from the hydroxylamine synthesis zone is fed with cyclohexanone to said cyclohexanone oxime synthesis zone wherein the hydroxylamine and the cyclohexanone react with each other to form cyclohexanone oxime, separating the cyclohexanone oxime and unreacted cyclohexanone from said solution and recycling said solution back to said hydroxylamine synthesis zone, stripping said solution being recycled from the cyclohexanone oxime synthesis zone to the hydroxylamine synthesis zone for a time sufficiently long enough so that residual amount of cyclohexanone and cyclohexanone oxime, present in the solution after removal of the cyclohexanone oxime produced in the cyclohexanone oxime synthesis zone, are substantially reduced to below about 0.02% by weight, the improvement of substantially preventing the poisoning of said palladium catalyst consisting in adding nitrate ions to the solution being recycled from the cyclohexanone oxime synthesis zone to the hydroxylamine synthesis zone after the stripping of said recycle solution.

* * * * *